(12) United States Patent
Festag et al.

(10) Patent No.: US 7,760,851 B2
(45) Date of Patent: Jul. 20, 2010

(54) DEVICE FOR NON-CONTACTING TRANSMISSION OF ELECTRICAL SIGNALS IN A COMPUTED TOMOGRAPHY SYSTEM

(75) Inventors: Mario Festag, Berlin (DE); Stefan Popescu, Erlangen (DE); Herbert Weithmann, Munich (DE)

(73) Assignees: Siemens Aktiengesellschaft, Munich (DE); Schleifring und Apparatebau GmbH, Fuerstenfeldbruck (DE)

( * ) Notice: Subject to any disclaimer, the term of this patent is extended or adjusted under 35 U.S.C. 154(b) by 0 days.

(21) Appl. No.: 12/394,855

(22) Filed: Feb. 27, 2009

(65) Prior Publication Data

US 2009/0220042 A1    Sep. 3, 2009

(30) Foreign Application Priority Data

Feb. 28, 2008    (DE) .................. 10 2008 011 594

(51) Int. Cl.
*A61B 6/00* (2006.01)
(52) U.S. Cl. ........................ 378/15; 378/21
(58) Field of Classification Search .......... 378/4–27, 378/193, 196, 197, 204, 210
See application file for complete search history.

(56) References Cited

U.S. PATENT DOCUMENTS 6,301,324 B1    10/2001    Pearson, Jr. et al. .......... 378/15

2007/0040635 A1    2/2007    Popescu et al. .......... 333/261

OTHER PUBLICATIONS

"Mikrowellentechnik," Hüthig (1984) pp. 84-89.
"Taschenbuch der Hochfrequenztechnik," Lange et al (1986), Chapter K.

*Primary Examiner*—Courtney Thomas
(74) *Attorney, Agent, or Firm*—Schiff Hardin LLP

(57) ABSTRACT

In a device for contact-free transmission of electrical signals between two gantry parts of a computed tomography system that rotate relative to one another, at least one annular, circumferential transmitter element is mounted on one gantry part to transmit the electrical signals, and at least one receiver element to receive the signals emitted by the transmitter element is mounted on the other gantry part. The transmitter element is formed by a single conductor running on a surface, this conductor representing an electrical reference ground (zero potential). At least one dielectric immediately follows on the surface, and multiple conductive conductor structure pairs are executed in two mirror-image parts and are mounted on the at least one dielectric. The separation of conductor structures arranged at the edge from the edge of the surface of the reference ground has a magnitude that both amounts to at least 10 mm and corresponds to at least half of the distance from the two conductor structures arranged in a mirror image at the edge, to the nearest conductor structure.

5 Claims, 3 Drawing Sheets

DEVICE FOR NON-CONTACTING TRANSMISSION OF ELECTRICAL SIGNALS IN A COMPUTED TOMOGRAPHY SYSTEM

BACKGROUND OF THE INVENTION

1. Field of the Invention

The present invention concerns a device for non-contacting (contact-free) transmission of electrical signals between two gantry parts of a computed tomography system that can rotate relative to one another, wherein at least one annular, circumferential transmitter element to transmit the electrical signals is arranged on one gantry part, and at least one receiver element to receive the signals emitted by the transmitter element is arranged on the other gantry part.

2. Description of the Prior Art

It is generally known that, in computed tomography using CT systems with continuously rotating gantries, the necessity exists to transmit both electrical power and electrical signals between the stationary portion of a gantry and the rotating portion of a gantry. Large electrical outputs are normally transferred with the use of slip contacts while electrical signals (as they are used in data transmission of detector data or of timing signals) are transmitted with the use of contact-free data transmission.

For example, European Patent Application EP 1 337 001 A1 and U.S. Pat. No. 6,301,324 describe such systems for contact-free transmission of electrical signals.

In the transmission of electrical signals with high frequency, the problem frequently exists that a large (often unacceptably large) proportion of perturbing radiation arises in the transmission paths so that it is difficult to comply with legal requirements, in particular when the transferred data rate rises sharply.

A circumferential ring with a special conductor structure attached therein that forms two traces arranged in a mirror image is frequently used for contact-free data transmission. For data transmission, these two differential conductor traces are alternatingly charged with differently polarized voltages (for example +5 volts and −5 volts). One polarity corresponds to a binary zero while the opposite polarity corresponds to a binary one. If higher data rates are to be transmitted, multiple mirror-image conductor structure pairs are used in parallel, in part due to the limited transmission capacity of such a conductor structure pair. It has been shown that a disproportionately sharp rise of EMC radiation (perturbing radiation) unexpectedly occurs. It is surmised that the positioning of the conductor structure pairs on the circumferential base structure is the reason for the unexpected rise of EMC radiation.

SUMMARY OF THE INVENTION

An object of the present invention is to provide a device for contact-free transmission of electrical signals between two gantry parts of a computed tomography system that can rotate relative to one another, the device emitting no excessive electromagnetic perturbing radiation even given the use of a number of conductor structure pairs for transmission of the data signals.

The invention is based on the insight that two significant errors that have led to significant, disproportionately high perturbing radiation have occurred in the design and the placement of the devices for contact-free data transmission using multiple conductor structure pairs with multiple data transmission paths.

One error source is that a separate base plate is conventionally used in part as an electrical reference ground for each transmitter in the design of the annular structure of the transmitter. Irregularities that occur in the installation of the entire system have led to problems due to the asymmetry produced thereby. It has turned out that the original intended cost savings of the use of modular design—one module per conductor structure pair with multiple modules given multiple conductor structure pairs—inadvertently produce disadvantageous effects.

A second error source is the placement of the conductor structure too close to the edge of the base plate, which likewise leads to problems in the symmetrical design, in particular when additional components are arranged at the edges that could serve in any way as a reference ground. The desire to have a large number of conductor structure traces for cost reasons has led to these traces being arranged ever closer to one another in parallel and near to the gantry frame, which leads to the disadvantages described above.

Therefore, in accordance with the invention, the annular structure that serves as a transmitter for the data transmission, and has multiple conductor structure pairs for the data transmission, is fashioned as one piece across the entire width on which the conductor structures are mounted, so that no symmetry disruptions can occur. Furthermore, the conductor structures that are mounted on the base plate with a dielectric as an intermediate layer must have a separation of at least 10 mm from the edge of the base. At the same time, this separation should amount to at least half of the free distance between the conductor structure pair at the edge and the nearest conductor structure pair.

If these aforementioned conditions are both satisfied, strong perturbing radiation can effectively be avoided.

Based on these basic requirements a device for contact-free transmission of electrical signals between two gantry parts of a computed tomography system that can rotate relative to one another has at least one annular, circumferential transmitter element that is mounted on one gantry part to transmit the electrical signals. At least one receiver element to receive the signals emitted by the transmitter element is mounted on the other gantry part. The transmitter element is formed by a single conductor running on a surface, which conductor represents an electrical reference ground (=zero potential), at least one dielectric immediately following on the surface and multiple conductive conductor structure pairs executed in two mirror-image parts, mounted on the at least one dielectric, these conductor structure pairs being reciprocally and alternatingly charged with the same voltage of opposite polarity for signal generation. The free separation (spacing) of conductor structures arranged at the edge from the edge of the surface of the reference ground has a magnitude that both amounts to at least 10 mm and corresponds to at least half of the free distance from the two conductor structures arranged in a mirror image at the edge to the nearest conductor structure.

In an embodiment of this device, the free distance of the conductor structure arranged at the edge from the edge of the surface of the reference ground can more precisely have a magnitude that lies between 10 mm and the free distance between the conductor structure pair arranged in a mirror image at the edge and the nearest conductor structure pair.

In a further embodiment of this device according to the invention, the plane on which the conductor structure pairs, the at least one dielectric and the reference ground are arranged represents a cylinder surface or alternatively is fashioned as a circular ring.

These aforementioned measures ensure that the emission of perturbing radiation does not occur even given slight installation differences since, under the circumstances, these installation differences are far removed from the region of the formed electrical fields formed by the conductor structure pairs.

The invention also encompassed a computed tomography system with a gantry to accommodate components rotating around a system axis, wherein electrical signals are exchanged between the rotating components and function elements that are arranged in a stationary manner, by a device as described above for contact-free signal exchange.

DESCRIPTION OF THE PREFERRED EMBODIMENTS

Figure 1:
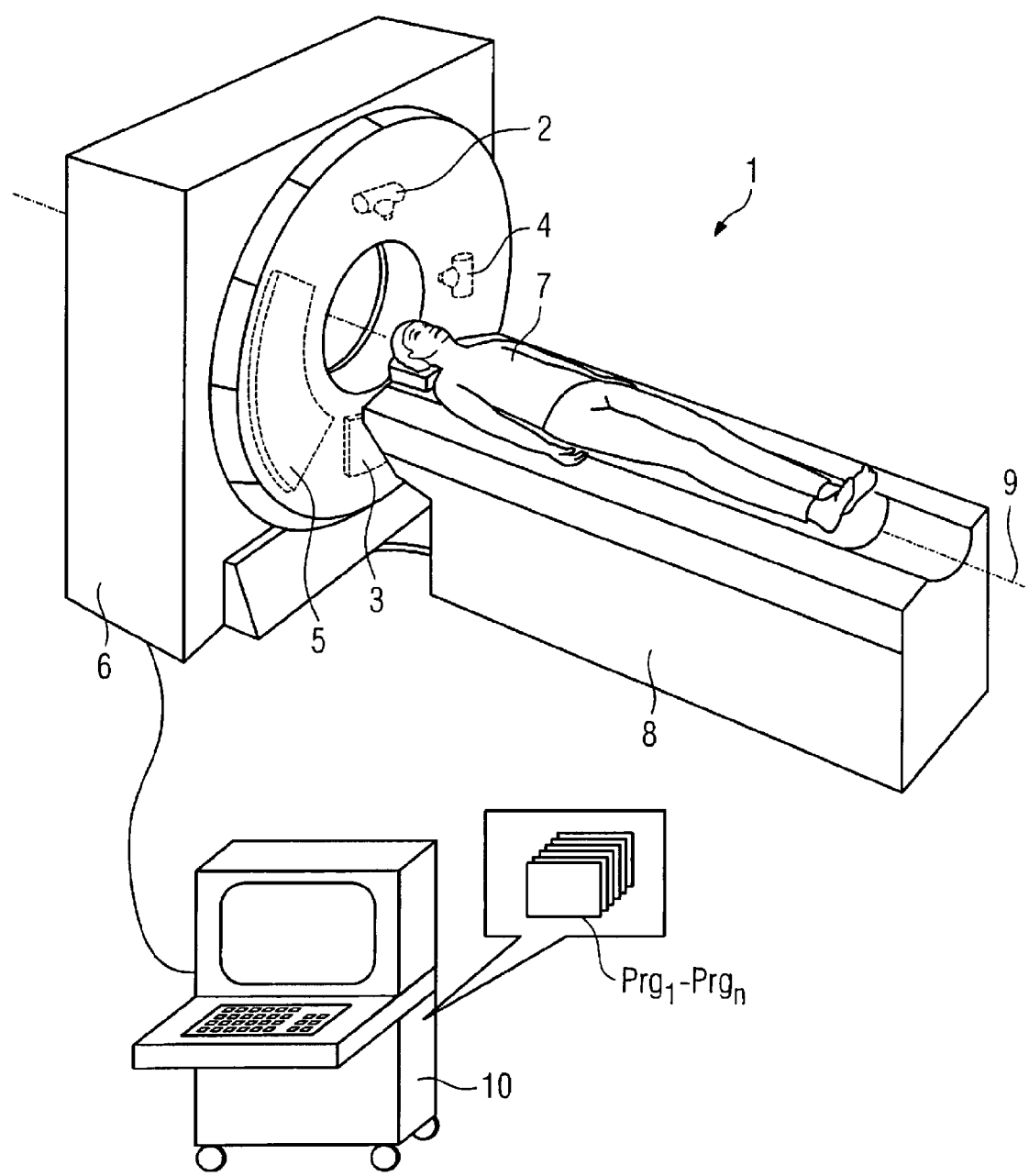
FIG. 1 schematically illustrates a CT system according to the invention.

FIG. 1 shows a computed tomography system 1 according to the invention with a gantry housing 6 in which a rotating gantry is located, on which a first tube/detector system, namely an x-ray tube 2 and a detector 3, is mounted. Alternatively, one or more additionally arranged tube/detector systems can be mounted, as are optionally shown with the x-ray tube 4 and the opposite detector 5. For an examination, a patient 7 is inserted into a measurement field by a patient bed 8 that is displaceable along the system axis 9 so that the absorption of the x-ray radiation can be measured from different projection angles. A computer 10 that is designed as a control and computation unit serves to control the CT system 1. Computer programs $Prg_1$ through $Prg_n$ that implement the control and the data evaluation (possibly including the reconstruction of the desired tomographical image data) are loaded in the computer 10.

It is necessary to transfer the large amount of incoming data via a contact-free path, in particular in the transfer of the detector data from the at least one detector to the rotating part of the gantry. For this purpose, a device according to the invention for contact-free transmission of electrical signals is mounted on the gantry so that these electrical signals can be transferred between the two gantry parts that can rotate relative to one another.

Figure 2:
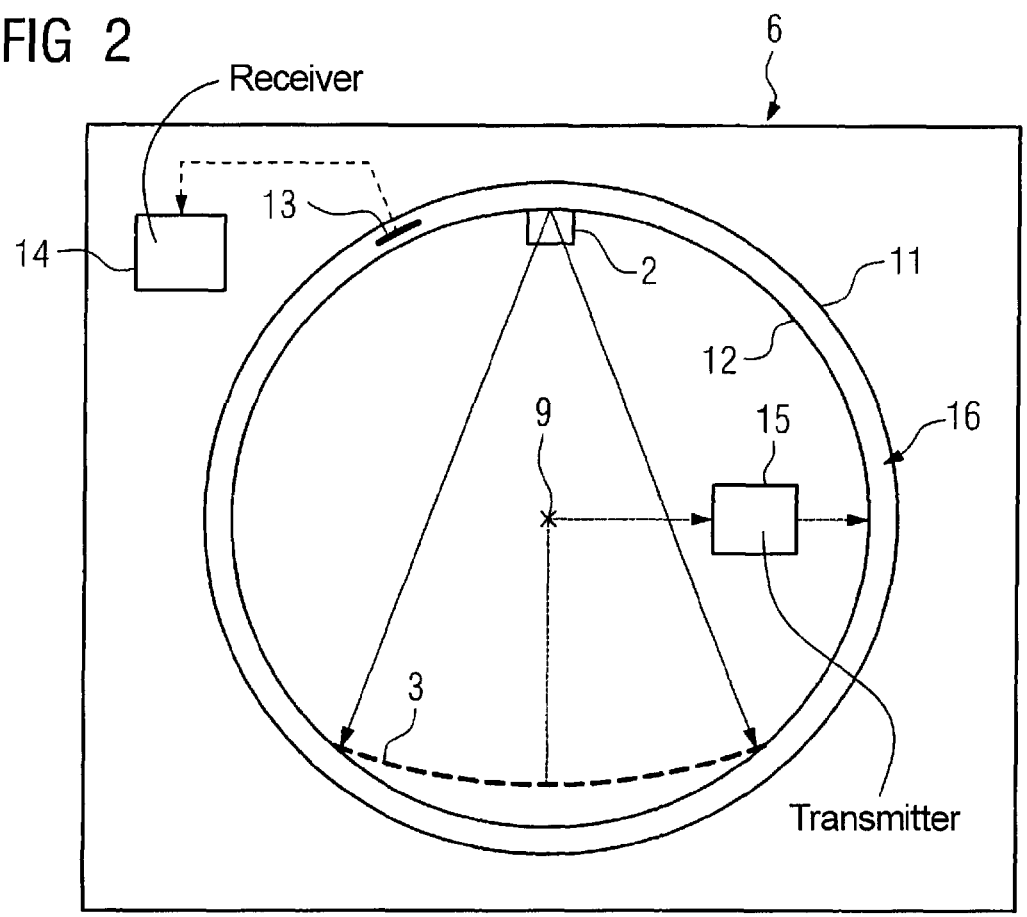
FIG. 2 is a schematic cross-section through the gantry in the CT system of FIG. 1.

A detailed view is presented in FIG. 2. This shows a cross-section perpendicular to the system axis 9 of the CT system through the gantry housing 6. The stator 11 of the gantry and the rotor 12 of the gantry rotating in the stator 11 are schematically shown in FIG. 2. An x-ray tube 2 with an opposite detector 3 is located on the rotor 12. Data produced by the detector 3 are transferred by a transmitter 15 to one or more annular transmission antennas arranged on the rotor 12. The emitted signals of this transmission antenna can be received by the reception antenna 13 that is mounted on the stationary part 11 of the gantry, and the signals can be evaluated by a receiver 14 and relayed to the computer system 10 (not shown here).

Figure 3:
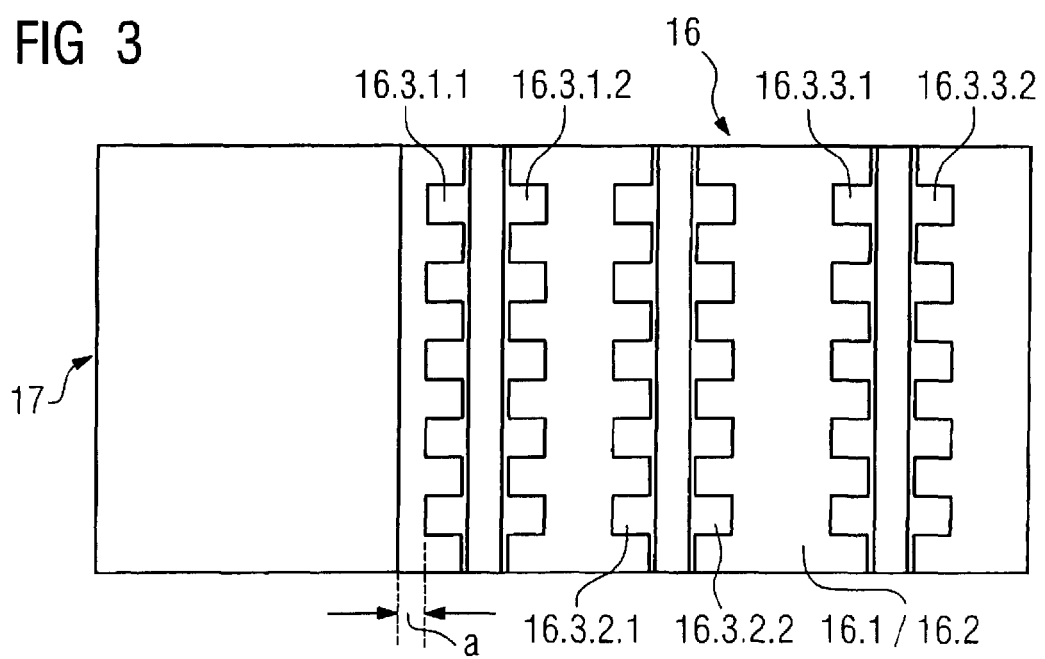
FIG. 3 is a view of a portion of a cylindrically fashioned surface with three conductor structures located thereon for data transmission.

In the embodiment of this CT system according to the invention, conductor structures as they are presented in detail in FIG. 3 serve as transmission antennas. FIG. 3 shows a section from the transmission antenna 16 according to the invention (here fashioned as a cylinder) in additional to a grounded component 17 of the rotating gantry. The transmission antenna 16 is formed by a plate (not recognizable in this plan view) serving as an electrical reference ground that is covered at least on one side by a connecting dielectric on which conductor structures fashioned in a mirror image are located in turn. These conductor structures fashioned in a mirror image are respectively present in pairs with the reference characters 16.3.1.1 and 16.3.1.2, 16.3.2.1 and 16.3.2.2, 16.3.3.1 and 16.3.3.2. Each pair forms a conductor structure pair in the sense of the invention, that acts as a transmitter.

For example, the two mirror-image structures arranged to the left transmit data signals with 2×2.5 Gbps while the mirror-image conductor structure pair arranged to the right serves to transmit a real-time signal with 1.5 Gbps.

Figure 4:
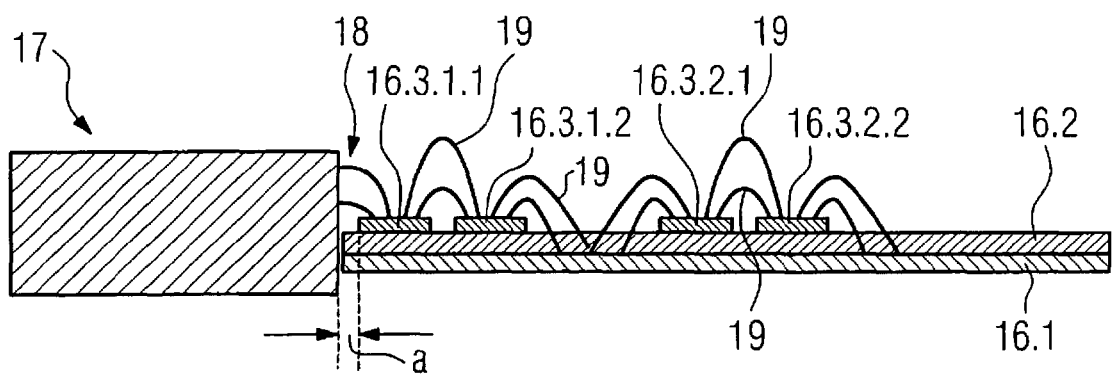
FIG. 4 is a cross-section through a device for contact-free transmission of electrical signals with conductor structure pairs arranged too thickly on the edge, as in the prior art.

A cross-section thereof is presented in FIG. 4. The grounded component 17 of the gantry is recognizable here to the left, and next to this a cross-section through the cylindrically fashioned surface (formed by conductive reference ground 16.1, oppositely-situated dielectric 16.2 and conductor structures 16.3.1.1 through 16.3.2.2 arranged on the dielectric 16.2) to the right.

For better comprehension, electrical field lines 19 emanating from the conductor structures are shown in FIG. 4 that are by and large formed symmetrically by the conductor structures. Only in the edge region 18 is possible that the field strength of the electrical field lines may be disrupted due to the proximity of component 17.

Disproportionately high electromagnetic perturbing radiation is radiated in the region 18 due to this disruption of the symmetry of the electrical field. The reason is that, under normal circumstances (thus when respective different voltages are alternately applied between the mirror-image conductor structure halves), although a measurable electromagnetic field exists in the short range, no radiation can be measured at a further range due to the symmetrically arranged polarity due to the opposite symmetrically arranged polarity given a symmetrical formation of the electromagnetic field. If this symmetry is disrupted for any reason (for example, due to an external component 17 coming into close proximity, or due to a non-uniformly applied electrical reference ground under the conductor structures), perturbing radiation is also emitted in remote regions.

Figure 5:
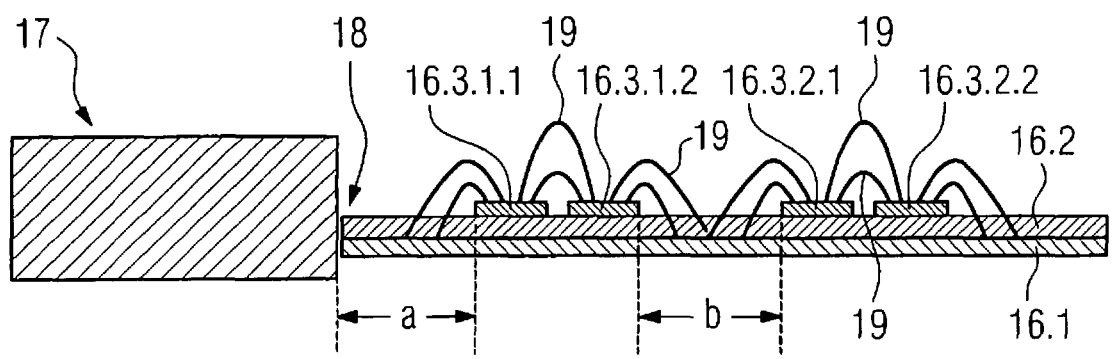
FIG. 5 is a cross-section according to FIG. 4, but with separation of the conductor structure pairs defined according to the invention.

In accordance with the invention, such symmetry disturbing influences are avoided (as shown in FIG. 5) by the electrical reference ground being fashioned as uniform and continuous below the conductor traces, and by the distance a between the conductor trace 16.3.1.1 arranged at the edge being at least 10 mm in the edge region 18 and, at the same time the distance also being greater than half the distance b between the conductor structure pair 16.3.1.1 and 16.3.1.2 arranged at the edge and the adjacent conductor structure pair 16.3.2.1 and 16.3.2.2.

The occurrence of electromagnetic radiation due to possible asymmetries in the electromagnetic field around the conductor structures can be avoided with this design so that the legal requirements with regard to electromagnetic compatibility can be satisfied, even given the use of multiple data transmission elements with a number of conductor structures.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for contact-free transmission of electrical signals between a stationary part and a rotatable part that rotates relative to the stationary part, said device comprising:
   - at least one annular circumferentially-proceeding transmitter element configured for mounting on said stationary part to transmit electrical signals;
   - at least one receiver element configured for mounting on said rotatable part to receive the electrical signals emitted by said transmitter element;
   - said transmitter element comprising a single conductor configured to run on a surface, said single conductor representing electrical reference ground, at least one dielectric immediately following said single conductor on said surface, and multiple conductive conductor structure pairs each being formed by two mirror-image components, mounted on said at least one dielectric, said conductor structure pairs being reciprocally and alternatingly charged with voltages of the same magnitude but opposite polarity for generating said electrical signals; and
   - said multiple conductive conductor structure pairs including an edge conductor structure pair that includes a conductor structure closest to an edge of said reference ground, said conductor structure that is closest to an edge of said reference ground being spaced from said edge of said reference ground by a distance having a magnitude that is at least 10 mm and that is at least half of a spacing between said edge conductor structure pair and another of said conductor structure pairs nearest to said edge conductor structure pairs.

2. A device as claimed in claim 1 wherein said distance has a magnitude between 10 mm and said distance between said edge conductor structure pair and the conductor structure pair nearest to said edge conductor structure pair.

3. A device as claimed in claim 1 wherein said surface is a cylindrical surface.

4. A device as claimed in claim 1 wherein said surface is a circular ring.

5. A computed tomography system comprising:
   - a gantry having a system axis, said gantry having a stationary part on which at least one component is mounted and a rotatable part that rotates around said system axis relative to said stationary part, said rotatable part having at least one further component mounted thereon; and
   - a device for contact-free transmission of electrical signals between said at least one component mounted on said stationary part and said at least one further component mounted on said rotatable part, said device comprising at least one annular circumferentially-proceeding transmitter element mounted on said stationary part to transmit electrical signals, at least one receiver element mounted on said rotatable part to receive the electrical signals emitted by said transmitter element, said transmitter element comprising a single conductor configured to run on a surface, said single conductor representing electrical reference ground, at least one dielectric immediately following said single conductor on said surface, and multiple conductive conductor structure pairs each being formed by two mirror-image components, mounted on said at least one dielectric, said conductor structure pairs being reciprocally and alternatingly charged with voltages of the same magnitude but opposite polarity for generating said electrical signals, and said multiple conductive conductor structure pairs including an edge conductor structure pair that includes a conductor closest to an edge of said reference ground, said conductor structure that is closest to the edge of said reference ground being spaced from said edge of said reference ground by a distance having a magnitude that is at least 10 mm and that at least half of a spacing between said edge conductor structure pair and another of said conductor structure pairs nearest to said edge conductor structure pairs.

* * * * *